United States Patent
Lee et al.

(10) Patent No.: US 9,522,961 B2
(45) Date of Patent: Dec. 20, 2016

(54) PROTEIN COMPLEXES AND METHODS OF MANUFACTURING BISPECIFIC ANTIBODIES USING THE PROTEIN COMPLEXES

(71) Applicant: Samsung Electronics Co., Ltd., Suwon-si, Gyeonggi-do (KR)

(72) Inventors: Jung-wook Lee, Yongin-si (KR); Min-Kyung Kim, Seoul (KR); Seon-hui Shim, Daegeon (KR); Jae-il Lee, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 118 days.

(21) Appl. No.: 14/023,538

(22) Filed: Sep. 11, 2013

(65) Prior Publication Data
US 2014/0073767 A1 Mar. 13, 2014

(30) Foreign Application Priority Data

Sep. 11, 2012 (KR) .......................... 10-2012-0100649

(51) Int. Cl.
| | |
|---|---|
| *C12P 21/00* | (2006.01) |
| *C07K 16/00* | (2006.01) |
| *C07K 16/46* | (2006.01) |
| *C07K 16/22* | (2006.01) |
| *C07K 16/28* | (2006.01) |
| *C12P 21/02* | (2006.01) |

(52) U.S. Cl.
CPC ............. *C07K 16/468* (2013.01); *C07K 16/22* (2013.01); *C07K 16/2863* (2013.01); *C12P 21/02* (2013.01); *C07K 2317/31* (2013.01); *C07K 2317/569* (2013.01); *C07K 2317/64* (2013.01); *C07K 2319/02* (2013.01); *C07K 2319/50* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 6,486,303 B1 | 11/2002 | Moyle | |
| 6,833,441 B2* | 12/2004 | Wang | ..................... C07K 16/00 424/130.1 |
| 7,951,917 B1 | 5/2011 | Arathoon et al. | |
| 8,227,577 B2 | 7/2012 | Klein et al. | |
| 2002/0155537 A1 | 10/2002 | Carter et al. | |
| 2003/0082801 A1* | 5/2003 | Barnes et al. | ................ 435/325 |
| 2003/0198956 A1* | 10/2003 | Makowski et al. | ............... 435/6 |
| 2004/0220388 A1 | 11/2004 | Mertens et al. | |
| 2011/0178279 A1 | 7/2011 | Williams et al. | |
| 2011/0229476 A1* | 9/2011 | Liu | ..................... A61K 47/484 424/136.1 |

FOREIGN PATENT DOCUMENTS

| | | |
|---|---|---|
| KR | 1020080013875 A | 2/2008 |
| KR | 1020100087397 A | 8/2010 |
| KR | 1020110068814 B1 | 7/2011 |
| WO | WO 2009/021754 A2 | 2/2009 |
| WO | WO 2011/034605 A2 | 3/2011 |
| WO | WO 2012/025530 A1 | 3/2012 |

OTHER PUBLICATIONS

Extended European Search Report for Application No. 13183787.4 mailed Jan. 2, 2014, 6 pages.

* cited by examiner

*Primary Examiner* — Julie Wu
(74) *Attorney, Agent, or Firm* — Leydig, Voit & Mayer, Ltd.

(57) ABSTRACT

A protein complex comprising (i) a first fusion protein comprising (a) a first polypeptide that comprises a first antigen-binding site and (b) a first binding protein linked to a terminus of the first polypeptide; and (ii) a second fusion protein comprising (a) a second polypeptide that comprises a second antigen-binding site and (b) a second binding protein linked to a terminus of the second polypeptide, wherein the protein complex comprises an amino acid sequence that enables cleavage between the first polypeptide and the first binding protein, and/or between the second polypeptide and the second binding protein, as well as a method for preparing a bi-specific antibody and related methods and compositions.

17 Claims, 2 Drawing Sheets

FIG. 1A

IN VITRO/VIVO
CLEAVAGE

FIG. 1B

SEQUENCE LISTING

```
<160> NUMBER OF SEQ ID NOS: 25

<210> SEQ ID NO 1
<211> LENGTH: 19
<212> TYPE: PRT
<213> ORGANISM: Artificial Sequence
<220> FEATURE:
<223> OTHER INFORMATION: Synthetic (secretion signal sequence)

<400> SEQUENCE: 1

Met Gly Trp Ser Cys Ile Ile Leu Phe Leu Val Ala Thr Ala Thr Gly
1               5                   10                  15

Val His Ser

<210> SEQ ID NO 2
<211> LENGTH: 57
<212> TYPE: DNA
<213> ORGANISM: Artificial Sequence
<220> FEATURE:
<223> OTHER INFORMATION: Synthetic

<400> SEQUENCE: 2
atgggctggt cctgcatcat cctgtttctg gtggccaccg ccaccggcgt gcactct         57

<210> SEQ ID NO 3
<211> LENGTH: 59
<212> TYPE: PRT
<213> ORGANISM: Artificial Sequence
<220> FEATURE:
<223> OTHER INFORMATION: Synthetic (GABAR1)

<400> SEQUENCE: 3

Glu Ala Gln Asp Thr Met Lys Thr Gly Ser Ser Thr Asn Asn Asn Glu
1               5                   10                  15

Glu Glu Lys Ser Arg Leu Leu Glu Lys Glu Asn Arg Glu Leu Glu Lys
            20                  25                  30

Ile Ile Ala Glu Lys Glu Glu Arg Val Ser Glu Leu Arg His Gln Leu
        35                  40                  45

Gln Ser Arg Gln Gln Leu Arg Ser Arg Arg His
    50                  55

<210> SEQ ID NO 4
<211> LENGTH: 177
<212> TYPE: DNA
<213> ORGANISM: Artificial Sequence
<220> FEATURE:
<223> OTHER INFORMATION: Synthetic

<400> SEQUENCE: 4
gaggcccagg acaccatgaa gaccggcagc agcaccaaca acaacgagga ggagaagagc      60
```

```
cgcctgctgg agaaggagaa ccgcgagctg gagaagatca tcgccgagaa ggaggagcgc    120
gtgagcgagc tgcgccacca gctgcagagc cgccagcagc tgcgcagccg ccgccac      177
```

<210> SEQ ID NO 5
<211> LENGTH: 48
<212> TYPE: PRT
<213> ORGANISM: Artificial Sequence
<220> FEATURE:
<223> OTHER INFORMATION: Synthetic (GABAR2)

<400> SEQUENCE: 5

```
Val Asn Gln Ala Ser Thr Ser Arg Leu Glu Gly Leu Gln Ser Glu Asn
1               5                   10                  15

His Arg Leu Arg Met Lys Ile Thr Glu Leu Asp Lys Asp Leu Glu Glu
            20                  25                  30

Val Thr Met Gln Leu Gln Asp Thr Pro Glu Lys Thr Thr Tyr Ile Lys
        35                  40                  45
```

<210> SEQ ID NO 6
<211> LENGTH: 144
<212> TYPE: DNA
<213> ORGANISM: Artificial Sequence
<220> FEATURE:
<223> OTHER INFORMATION: Synthetic

<400> SEQUENCE: 6

```
gtgaaccagg ccagcaccag ccgcctggag ggcctgcaga gcgagaacca ccgcctgcgc    60
atgaagatca ccgagctgga caaggacctg gaggaggtga ccatgcagct gcaggacacc   120
cccgagaaga ccacctacat caag                                          144
```

<210> SEQ ID NO 7
<211> LENGTH: 6
<212> TYPE: PRT
<213> ORGANISM: Artificial Sequence
<220> FEATURE:
<223> OTHER INFORMATION: Synthetic (Furin cleavage peptide)

<400> SEQUENCE: 7

```
Arg Gly Arg Lys Arg Arg
1               5
```

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8

```
cgcggccgca agcgccgc                                                  18
```

<210> SEQ ID NO 9
<211> LENGTH: 108
<212> TYPE: PRT
<213> ORGANISM: Artificial Sequence
<220> FEATURE:
<223> OTHER INFORMATION: Synthetic (single-domain antibody with the
      binding site to vascular endothelial growth factor)

<400> SEQUENCE: 9

```
Asp Ile Gln Met Thr Gln Ser Pro Ser Ser Leu Ser Ala Ser Val Gly
1               5                   10                  15
```

-continued

Asp Arg Val Thr Ile Thr Cys Arg Ala Ser Gln Lys Ile Phe Asn Gly
            20                  25                  30

Leu Ser Trp Tyr Gln Gln Lys Pro Gly Lys Ala Pro Lys Leu Leu Ile
        35                  40                  45

Tyr His Ser Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu Leu Tyr Pro Tyr
                85                  90                  95

Thr Phe Gly Gln Gly Thr Lys Val Glu Ile Lys Arg
            100                 105

<210> SEQ ID NO 10
<211> LENGTH: 324
<212> TYPE: DNA
<213> ORGANISM: Artificial Sequence
<220> FEATURE:
<223> OTHER INFORMATION: Synthetic

<400> SEQUENCE: 10
gatatccaga tgacccagag ccccagcagc ctgtctgcct ctgtgggcga cagagtgacc      60
atcacctgtc gggccagcca aagatcttc aacggcctga gctggtatca gcagaagccc     120
ggcaaggccc ccaagctgct gatctaccac agcagcaccc tgcagagcgg cgtgccaagc     180 agatttctg gcagcggcag cggcaccgac ttcaccctga caatcagcag cctgcagccc     240
gaggacttcg ccacctacta ctgccagcag gtcctgctgt accccaacac ctttggccag     300
ggcaccaagg tggaaatcaa gaga                                            324

<210> SEQ ID NO 11
<211> LENGTH: 108
<212> TYPE: PRT
<213> ORGANISM: Artificial Sequence
<220> FEATURE:
<223> OTHER INFORMATION: Synthetic (single-domain antibody with the
      binding site to epidermal growth factor receptor 2)

<400> SEQUENCE: 11

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Trp Ile Gly Asn Leu
            20                  25                  30

Leu Asp Trp Tyr Gln Gln Lys Pro Gly Glu Ala Pro Lys Leu Leu Ile
        35                  40                  45

Tyr Tyr Ala Ser Phe Leu Gln Ser Gly Val Pro Ser Arg Phe Ser Gly
    50                  55                  60

Gly Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105

<210> SEQ ID NO 12
<211> LENGTH: 324
<212> TYPE: DNA
<213> ORGANISM: Artificial Sequence
<220> FEATURE:
<223> OTHER INFORMATION: Synthetic

<400> SEQUENCE: 12

```
gacattcaga tgacacagtc ccccacctcc ctgtctgcca gcgtgggaga tcgcgtgacc      60
attacctgca gagcctccca gtggatcggc aacctgctgg attggtatca gcagaaacct    120
ggggaggctc ctaaactgct gatctattac gccagcttcc tgcagtccgg cgtgccctct    180
agattttccg gcggaggctt cggcacagat tcacactga ccatctcatc cctgcagcct    240
gaagattttg ccacatatta ttgccagcag gccaaccctg ccccctgac atttggacag    300 ggaacaaagg tcgagatcaa gcgc                                           324
```

<210> SEQ ID NO 13
<211> LENGTH: 232
<212> TYPE: PRT
<213> ORGANISM: Artificial Sequence
<220> FEATURE:
<223> OTHER INFORMATION: Synthetic (hinge- CH2-CH3)

<400> SEQUENCE: 13

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 14
<211> LENGTH: 696
<212> TYPE: DNA
<213> ORGANISM: Artificial Sequence
<220> FEATURE:
<223> OTHER INFORMATION: Synthetic

<400> SEQUENCE: 14

```
gagcctaagt cctgtgacaa gacacacaca tgccctccct gcccagcccc agaactgctc    60
ggtggaccct ctgtgtttct gtttccaccc aagcctaagg atacactcat gatctccaga   120
acacctgaag tgacatgtgt ggtcgtcgac gtgtcacatg aggatccaga agtcaagttt   180
aactggtatg tggatggggt cgaggtgcac aatgccaaaa caaaacctcg ggaagaacag   240
tataattcca cctatagagt cgtgtctgtg ctcaccgtgc tccatcagga ttggctcaat   300
gggaagaat  acaaatgtaa agtctctaac aaagccctgc cgctcctat  cgaaaagaca   360
atctccaagg ccaaggaca  gcctcgcgag cctcaggtct acaccctgcc accttcccgc   420
gaggaaatga caaaaaatca ggtgtcactc acctgtctcg tgaagggtt  ttacccctcc   480
gacattgccg tcgagtggga gtccaatgga cagcccgaga caattataa  gacaacacct   540
cccgtcctgg actccgatgg atcatttttt ctgtactcca agctcaccgt cgataagtcc   600
agatggcagc agggaaatgt cttttcctgc tccgtgatgc atgaagctct ccacaatcat   660
tacacacaga aaagcctgtc cctgtccccc ggcaag                             696
```

<210> SEQ ID NO 15
<211> LENGTH: 405
<212> TYPE: PRT
<213> ORGANISM: Artificial Sequence
<220> FEATURE:
<223> OTHER INFORMATION: Synthetic (fusion protein)

<400> SEQUENCE: 15

```
Glu Ala Gln Asp Thr Met Lys Thr Gly Ser Ser Thr Asn Asn Asn Glu
1               5                   10                  15

Glu Glu Lys Ser Arg Leu Leu Glu Lys Glu Asn Arg Glu Leu Glu Lys
            20                  25                  30

Ile Ile Ala Glu Lys Glu Glu Arg Val Ser Glu Leu Arg His Gln Leu
        35                  40                  45

Gln Ser Arg Gln Gln Leu Arg Ser Arg Arg His Arg Gly Arg Lys Arg
    50                  55                  60

Arg Asp Ile Gln Met Thr Gln Ser Pro Ser Ser Leu Ser Ala Ser Val
65                  70                  75                  80

Gly Asp Arg Val Thr Ile Thr Cys Arg Ala Ser Gln Lys Ile Phe Asn
                85                  90                  95

Gly Leu Ser Trp Tyr Gln Gln Lys Pro Gly Lys Ala Pro Lys Leu Leu
            100                 105                 110

Ile Tyr His Ser Ser Thr Leu Gln Ser Gly Val Pro Ser Arg Phe Ser
        115                 120                 125

Gly Ser Gly Ser Gly Thr Asp Phe Thr Leu Thr Ile Ser Ser Leu Gln
    130                 135                 140

Pro Glu Asp Phe Ala Thr Tyr Tyr Cys Gln Gln Val Leu Leu Tyr Pro
145                 150                 155                 160

Tyr Thr Phe Gly Gln Gly Thr Lys Val Glu Ile Lys Arg Glu Pro Lys
                165                 170                 175

Ser Cys Asp Lys Thr His Thr Cys Pro Pro Cys Pro Ala Pro Glu Leu
            180                 185                 190

Leu Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
    210                 215                 220

Ser His Glu Asp Pro Glu Val Lys Phe Asn Trp Tyr Val Asp Gly Val
225                 230                 235                 240
```

```
Glu Val His Asn Ala Lys Thr Lys Pro Arg Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Pro Ala
        275                 280                 285

Pro Ile Glu Lys Thr Ile Ser Lys Ala Lys Gly Gln Pro Arg Glu Pro
    290                 295                 300

Gln Val Tyr Thr Leu Pro Pro Ser Arg Glu Glu Met Thr Lys Asn Gln
305                 310                 315                 320

Val Ser Leu Thr Cys Leu Val Lys Gly Phe Tyr Pro Ser Asp Ile Ala
                325                 330                 335

Val Glu Trp Glu Ser Asn Gly Gln Pro Glu Asn Asn Tyr Lys Thr Thr
            340                 345                 350

Pro Pro Val Leu Asp Ser Asp Gly Ser Phe Phe Leu Tyr Ser Lys Leu
        355                 360                 365

Thr Val Asp Lys Ser Arg Trp Gln Gln Gly Asn Val Phe Ser Cys Ser
    370                 375                 380

Val Met His Glu Ala Leu His Asn His Tyr Thr Gln Lys Ser Leu Ser
385                 390                 395                 400

Leu Ser Pro Gly Lys
            405

<210> SEQ ID NO 16
<211> LENGTH: 1224
<212> TYPE: DNA
<213> ORGANISM: Artificial Sequence
<220> FEATURE:
<223> OTHER INFORMATION: Synthetic

<400> SEQUENCE: 16
gaggcccagg acaccatgaa gaccggcagc agcaccaaca caacgagga ggagaagagc      60 cgcctgctgg agaaggagaa ccgcgagctg gagaagatca tcgccgagaa ggaggagcgc     120
gtgagcgagc tgcgccacca gctgcagagc cgccagcagc tgcgcagccg ccgccaccgc     180
ggccgcaagc gccgcgatat ccagatgacc cagagcccca gcagcctgtc tgcctctgtg     240
ggcgacagag tgaccatcac ctgtcgggcc agccagaaga tcttcaacgg cctgagctgg     300
tatcagcaga agcccggcaa ggcccccaag ctgctgatct accacagcag caccctgcag     360
agcggcgtgc caagcagatt ttctggcagc ggcagcggca ccgacttcac cctgacaatc     420
agcagcctgc agcccgagga cttcgccacc tactactgcc agcaggtcct gctgtacccc     480
tacacctttg gccagggcac caaggtggaa atcaagagag agcccaagag ctgcgacaag     540
acccacacct gtccccttg tcctgcccct gaactgctgg gaggcctag cgtgttcctg      600 ttccccccaa agcccaagga caccctgatg atcagccgga cccccgaagt gacctgcgtg     660
gtggtggatg tgtcccacga ggaccctgaa gtgaagttca attggtacgt ggacggcgtg     720
gaagtgcaca acgccaagac caagccccag aggaacagt acaacagcac ctaccgggtg      780
gtgtccgtgc tgacagtgct gcaccaggac tggctgaacg gcaaagagta caagtgcaag     840
gtgtccaaca aggccctgcc tgcccccatc gagaaaacca tcagcaaggc caagggccag     900
cccagagaac ccaggtgta cacactgccc ccagcagag aagagatgac caagaaccag      960
gtgtccctga cctgcctggt caagggcttc taccccagcg atatcgccgt ggaatgggag    1020
agcaacggcc agcctgagaa caactacaag accacccccc ctgtgctgga cagcgacggc    1080
```

```
tcattcttcc tgtacagcaa gctgaccgtg gacaagagcc ggtggcagca gggcaacgtg    1140
ttcagctgca gcgtgatgca cgaggccctg cacaaccact acacccagaa gtccctgagc    1200
ctgagccccg gcaagtgact cgag                                            1224
```

<210> SEQ ID NO 17
<211> LENGTH: 394
<212> TYPE: PRT
<213> ORGANISM: Artificial Sequence
<220> FEATURE:
<223> OTHER INFORMATION: Synthethic (fusion protein)

<400> SEQUENCE: 17

```
Val Asn Gln Ala Ser Thr Ser Arg Leu Glu Gly Leu Gln Ser Glu Asn
1               5                   10                  15

His Arg Leu Arg Met Lys Ile Thr Glu Leu Asp Lys Asp Leu Glu Glu
            20                  25                  30

Val Thr Met Gln Leu Gln Asp Thr Pro Glu Lys Thr Thr Tyr Ile Lys
        35                  40                  45

Arg Gly Arg Lys Arg Arg Asp Ile Gln Met Thr Gln Ser Pro Thr Ser
    50                  55                  60

Leu Ser Ala Ser Val Gly Asp Arg Val Thr Ile Thr Cys Arg Ala Ser
65                  70                  75                  80

Gln Trp Ile Gly Asn Leu Leu Asp Trp Tyr Gln Gln Lys Pro Gly Glu
                85                  90                  95

Ala Pro Lys Leu Leu Ile Tyr Tyr Ala Ser Phe Leu Gln Ser Gly Val
            100                 105                 110

Pro Ser Arg Phe Ser Gly Gly Gly Phe Gly Thr Asp Phe Thr Leu Thr
        115                 120                 125

Ile Ser Ser Leu Gln Pro Glu Asp Phe Ala Thr Tyr Tyr Cys Gln Gln
    130                 135                 140

Ala Asn Pro Ala Pro Leu Thr Phe Gly Gln Gly Thr Lys Val Glu Ile
145                 150                 155                 160

Lys Arg Glu Pro Lys Ser Cys Asp Lys Thr His Thr Cys Pro Pro Cys
                165                 170                 175

Pro Ala Pro Glu Leu Leu Gly Gly Pro Ser Val Phe Leu Phe Pro Pro
            180                 185                 190

Lys Pro Lys Asp Thr Leu Met Ile Ser Arg Thr Pro Glu Val Thr Cys
        195                 200                 205

Val Val Val Asp Val Ser His Glu Asp Pro Glu Val Lys Phe Asn Trp
    210                 215                 220

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Lys Val Ser Asn
            260                 265                 270

Lys Ala Leu Pro Ala Pro Ile Glu Lys Thr Ile Ser Lys Ala Lys Gly
        275                 280                 285

Gln Pro Arg Glu Pro Gln Val Tyr Thr Leu Pro Ser Arg Glu Glu
    290                 295                 300

Met Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335
```

Asn Tyr Lys Thr Thr Pro Pro Val Leu Asp Ser Asp Gly Ser Phe Phe
              340                 345                 350

Leu Tyr Ser Lys Leu Thr Val Asp Lys Ser Arg Trp Gln Gln Gly Asn
          355                 360                 365

Val Phe Ser Cys Ser Val Met His Glu Ala Leu His Asn His Tyr Thr
      370                 375                 380

Gln Lys Ser Leu Ser Leu Ser Pro Gly Lys
385                 390

<210> SEQ ID NO 18
<211> LENGTH: 1191
<212> TYPE: DNA
<213> ORGANISM: Artificial Sequence
<220> FEATURE:
<223> OTHER INFORMATION: Synthetic

<400> SEQUENCE: 18

```
gtgaaccagg ccagcaccag ccgcctggag ggcctgcaga gcgagaacca ccgcctgcgc     60
atgaagatca ccgagctgga caaggacctg gaggaggtga ccatgcagct gcaggacacc    120
cccgagaaga ccacctacat caagcgcggc cgcaagcgcc gcgacattca gatgacacag    180
tccccacct ccctgtctgc cagcgtggga gatcgcgtga ccattacctg cagagcctcc    240
cagtggatcg gcaacctgct ggattggtat cagcagaaac tggggaggc tcctaaactg    300
ctgatctatt acgccagctt cctgcagtcc ggcgtgccct ctagattttc cggcggaggc    360
ttcggcacag atttcacact gaccatctca tccctgcagc ctgaagattt tgccacatat    420
tattgccagc aggccaaccc tgcccccctg acatttggac agggaacaaa ggtcgagatc    480
aagcgcgagc ctaagtcctg tgacaagaca cacacatgcc ctccctgccc agccccagaa    540
ctgctcggtg gaccctctgt gtttctgttt ccacccaagc ctaaggatac actcatgatc    600
tccagaacac ctgaagtgac atgtgtggtc gtcgacgtgt cacatgagga tccagaagtc    660
aagtttaact ggtatgtgga tggggtcgag gtgcacaatg ccaaaacaaa acctcgggaa    720
gaacagtata attccaccta tagagtcgtg tctgtgctca ccgtgctcca tcaggattgg    780
ctcaatggga agaatacaa atgtaaagtc tctaacaaag ccctgccgc tcctatcgaa    840
aagacaatct ccaaggccaa aggacagcct cgcgagcctc aggtctacac cctgccacct    900
tcccgcgagg aaatgacaaa aatcaggtg tcactcacct gtctcgtgaa ggggttttac    960
ccctccgaca ttgccgtcga gtgggagtcc aatggacagc ccgagaacaa ttataagaca   1020
acacctcccg tcctggactc cgatggatca ttttttctgt actccaagct caccgtcgat   1080
aagtccagat ggcagcaggg aaatgtcttt tcctgctccg tgatgcatga agctctccac   1140
aatcattaca cacagaaaag cctgtccctg tccccggca agtgactcga g             1191
```

<210> SEQ ID NO 19
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 19

Arg Xaa Arg Arg
1

```
<210> SEQ ID NO 20
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 20

Arg Xaa Lys Arg
1

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Ser Cys Pro Ile Lys Glu
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic

<400> SEQUENCE: 22

Ile Glu Gly Arg
1

<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23

Ile Asp Gly Arg
1

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Glu Asn Leu Tyr Phe Gln Glu
1               5

<210> SEQ ID NO 25
<211> LENGTH: 7
<212> TYPE: PRT
```

```
<213> ORGANISM: Artificial Sequence
<220> FEATURE:
<223> OTHER INFORMATION: Synthetic

<400> SEQUENCE: 25

Glu Asn Leu Tyr Phe Gln Ser
1               5
```

PROTEIN COMPLEXES AND METHODS OF MANUFACTURING BISPECIFIC ANTIBODIES USING THE PROTEIN COMPLEXES

CROSS-REFERENCE TO RELATED APPLICATION

This application claims the benefit of Korean Patent Application No. 10-2012-0100649, filed on 11 Sep. 2012 in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 21,207 Byte ASCII (Text) file named "713535_ST25.TXT," created on Sep. 9, 2013.

BACKGROUND

1. Field

The present disclosure relates to protein complexes and methods of preparing bispecific antibodies using the protein complexes.

2. Description of the Related Art

Monoclonal antibodies have become a leader of new drugs in the market and, accordingly, are being developed as drugs for a variety of targets. However, in many cases, the development of new drugs is limited; for example, there is no satisfactory efficacy, it is expensive to produce antibodies, or the like. As a one solution to overcome these problems, studies of bispecific antibodies have been steadily explored since the mid-1980s, but in spite of a large effort, a dominant technology has not appeared yet.

In a conventional method of preparing bispecific antibodies, there are difficulties in mass production of homogeneous bispecific antibodies difficulties due to low efficacy and side effects. In recent years, a competitive new antibody platform has appeared based on the strength of the development of antibody engineering technology, but it is still in the verification phase.

Therefore, even by conventional technology, the development of a new protein complex having specificity to at least two heterogeneous antigens is necessary.

SUMMARY

Provided are protein complexes to prepare bispecific antibodies. In particular, the invention provides a protein complex comprising: (i) a first fusion protein comprising (a) a first polypeptide that comprises a first antigen-binding site and (b) a first binding protein that is linked to the terminus of the first polypeptide; and (ii) a second fusion protein comprising (a) a second polypeptide that comprises a second antigen-binding site and (b) a second binding protein that is linked to the terminus of the second polypeptide, wherein the protein complex comprises amino acid sequences that enable cleavage between the first polypeptide and the first binding protein, and/or between the second polypeptide and the second binding protein.

Provided are polynucleotides that encode the protein complexes, recombinant vectors that include the polynucleotides, and host cells that include the recombinant vectors.

Provided are methods of preparing bispecific antibodies using the protein complexes.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items According to an aspect of the present invention, a protein complex comprising a first fusion protein and a second fusion protein is provided. The first fusion protein comprises a first polypeptide that includes a first antigen-binding site and a first binding protein that is linked to the terminus of the first polypeptide. The second fusion protein comprises a second polypeptide that includes a second antigen-binding site and a second binding protein that is linked to the terminus of the second polypeptide. In addition, the protein complex comprises amino acid sequences that enable cleavage between the first polypeptide and the first binding protein, or between the second polypeptide and the second binding protein.

The terminology "antigen-binding site" used herein refers to a site where an antigen or an epitope binds to in an immunoglobulin molecule. The antigen-binding site may include a complementarity determining region (CDR). A CDR refers to amino acid sequences of a hypervariable region in a heavy chain and a light chain of an immunoglobulin. The heavy chain and the light chain each may include three CDRs (CDRH1, CDRH2, CDRH3 and CDRL1, CDRL2, CDRL3), and the CDRs may provide contact residues that are important for binding of an antibody to an antigen or an epitope. The terminology "heavy chain" used herein refers to a whole heavy chain that includes a variable region domain $V_H$ including amino acid sequences with sufficient variable region sequences to provide specificity to the antigen and three constant region domains CH1, CH2, and CH3, and a fragment thereof. The terminology "light chain" refers to a whole light chain that includes a variable region domain $V_L$ including amino acid sequences with sufficient variable region sequences to provide specificity to the antigen and a constant region domain $C_L$, and a fragment thereof.

According to an embodiment of the present invention, the first antigen-binding site and the second antigen-binding site may be positioned at the N-terminus of the first polypeptide and the second polypeptide, respectively.

According to another embodiment of the present invention, the first antigen-binding site and the second antigen-binding site may be identical to, or different from, each other. When the first antigen-binding site and the second antigen-binding site are identical to each other, the protein complex may be used as a monoclonal antibody. When the first antigen-binding site and the second antigen-binding site are different from each other, the protein complex may be used as a bispecific antibody. Examples of antigens that may be bound to the first antigen-binding site and/or the second antigen-binding site may be selected from the group consisting of DLL4, VEGFR2, Notch1, Notch2, Notch3, Notch4, Notch(pan), JAG1, JAG2, DLL(pan), JAG(pan), ERBB(pan), c-Met, IGF-1R, PDGFR, Patched, Hedgehog family polypeptides, Hedgehog(pan), WNT family polypeptides, WNT(pan), FZD1, FZD2, FZD3, FZD4, FZD5, FZD6, FZD7, FZD8, FZD9, FZD10, FZD(pan), LRP5, LRP6, CD20, IL-17, CD86, Muc16, PSCA, CD44, c-Kit, DDR1, DDR2, RSPO1, RSPO2, RSPO3, RSPO4, RSPO(pan), BMP family polypeptides, BMP(pan), BMPR1a, BMPR1b, and a combination thereof, but are not limited thereto. In addition, examples of antigens that may be bound to the antigen-binding sites may be selected from the group consisting of EpCAM, tumor-associated glycoprotein-72 (TAG-72), tumor-associated antigen CA 125, prostate specific membrane antigen (PSMA), high molecular weight melanoma-associated antigen (HMW-MAA), tumor-associated antigen expressing Lewis Y related carbohydrate, carcinoembryonic antigen (CEA), CEACAM5, HMFG PEM, mucin MUC1, MUC18 and a cytokeratin tumor-associated antigen, a bacterial antigen, a viral antigen, an allergen, a fluorescein, a lysozyme, toll-like receptor 9, an erythropoietin, CD2, CD3, CD3E, CD4, CD11, CD11a, CD14, CD18, CD19, CD20, CD22, CD23, CD25, CD28, CD29, CD30, CD33 (protein p67), CD38, CD40, CD40L, CD52, CD54, CD56, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma, TNF-alpha, TNF-beta2, TNF-beta, TNF-alpha/beta, TNF-R1, TNF-R11, FasL, CD27L, CD30L, 4-1 BBL, TRAIL, RANKL, TWEAK, APRIL, BAFF, LIGHT, VEG1, OX40L, TRAIL receptor-1, A1 adenosine receptor, lymphotoxin beta receptor, TACI, BAFF-R, EPO, LFA-3, ICAM-1, ICAM-3, integrin beta1, integrin beta2, integrin alpha4/beta7, integrin alpha2, integrin alpha3, integrin alpha4, integrin alpha5, integrin alpha6, integrin alpha V, integrin alpha V beta3, FGFR-3, keratinocyte growth factor, VLA-1, VLA-4, L-selectin, anti-Id, E-selectin, HLA, HLADR, CTLA-4, a T cell receptor, B7-1, B7-2, VNR integrin, TGFbeta1, TGFbeta2, eotaxin1, B-lymphocyte stimulator (BLyS), complement C5, IgE, factor VII, CD64, CBL, NCA 90, EGFR (ErbB-1), Her2/neu (ErbB-2), Her3 (ErbB-3), Her4 (ErbB4), a tissue factor, VEGF, VEGFR, an endothelin receptor, VLA-4, and a carbohydrate such as a blood group antigen or a related carbohydrate, a galilee-glycosylation, a gastrin, a gastrin receptor, a tumor-related carbohydrate, hapten NP-cap or NIP-cap, T cell receptor alpha/beta, E-selectin, digoxin, placental alkaline phosphatase (PLAP) and testicular PLAP-similar alkaline phosphatase, a transferring receptor, heparanase I, human cardiac myosin, glycoprotein IIb/IIIa (GPIIb/IIIa), human cytomegalovirus (HCMV) gH envelope glycoprotein, HIV gp120, HCMV, respiratory syncitial virus (RSV) F, RSVF Fgp, VNR integrin, Hep B gp120, CMV, gpIIbIIIa, HIV IIIB gp120 V3 loop, RSV Fgp, Herpes simplex virus (HSV) gD glycoprotein, HSV gB glycoprotein, HCMV gB envelope glycoprotein, *Clostridium perfringens* toxin and a fragment thereof, but are not limited thereto.

According to another embodiment of the present invention, the first binding protein and the second binding protein of the protein complex may specifically bind to each other.

The terminology "binding protein" used herein refers to a group of proteins that may specifically bind by interaction between two or more proteins. The first binding protein and the second binding protein that specifically bind may form a heterodimer, and the binding proteins that form the heterodimer may be secreted outside a cell after forming the heterodimer in the cell. Examples of the first binding protein and the second binding protein that form the heterodimer each may be any one selected from the group consisting of GABAR1 and GABAR2; Jun and Fos; Lin7 and Lin2C; GABAR1 and GABAR2; c-Myc and Max; ATF4 and EBP; Pop5 and Rpp1; ErbB1 and ErbB2; RXR and PPARγ; RXR and TR; AP3 and PI; MDM2 and MDMX; SRP9 and SRP14; p50 and p65; TLR1 and TLR2; IMβ and IM7; TAP and p15; and p40 and p67, but are not limited thereto.

In a typical process of an intracellular antibody formation, a dimer is formed by interaction between fragment crystallizable (Fc) regions of the two heavy chains. However, in the process of preparing a bispecific antibody, there is a similar probability of forming a homodimer and a heterodimer, according to the process described above. Thus, forming efficiency of a bispecific antibody may be lowered. The first binding protein and the second binding protein are presented to improve the forming efficiency of a bispecific antibody in particular.

According to another embodiment of the present invention, the amino acid sequences that enable cleavage may be any amino acid sequences, such that first binding protein, the first polypeptide, the second binding protein, and the second polypeptide are not cleaved. The amino acid sequences that enable cleavage may be confirmed by searching through a database known to one of ordinary skill in the art. For example, protease that is found in www.expasy.org/tools/peptidecutter/peptidecutter enzymes.html or its amino acid sequence that enables cleavage may be used. In addition, examples of the protease that enable cleavage are furin, calpain, factor X (FXa), tobacco etch virus (TEV) protease, and proprotein convertase (PC) family, but are not limited thereto. For example, amino acid sequences that are cleaved by furin may be Arg-X-Arg-Arg (SEQ ID NO: 19) or Arg-X-Lys-Arg (SEQ ID NO: 20); amino acid sequences that are cleaved by calpain may be Ser-Cys-Pro-Ile-Lys-Glu (SEQ ID NO: 21); amino acid sequences that are cleaved by factor X may be Ile-Glu-Gly-Arg (SEQ ID NO: 22) or Ile-Asp-Gly-Arg (SEQ ID NO: 23); and amino acid sequences that are cleaved by TEV protease may be Glu-Asn-Leu-Tyr-Phe-Gln-Glu (SEQ ID NO: 24) or Glu-Asn-Leu-Tyr-Phe-Gln-Ser (SEQ ID NO: 25).

According to another embodiment of the present invention, the polypeptide including the antigen-binding site may include a single-domain antibody, Fab2-Fc, scFv-Fc, Ab-Fc domain, a nanobody, a minibody, an IgG type, an Fc region, or a combination thereof.

In one embodiment, the protein fusion complex may comprise, consist essentially of, or consist of the amino acid sequence of SEQ ID NO: 15 or 17.

According to another aspect of the present invention, a polynucleotide that encodes the protein complex is included.

The terminology "polynucleotide" used herein refers to a polymer of deoxyribose or ribonucleotide in the form of a single-strand or a double-strand. The polynucleotide includes RNA genome sequences, DNA (genomic DNA and complementary DNA), and RNA sequences that are transcribed therefrom. Unless stated otherwise, the polynucleotide includes analogs of the natural polynucleotide.

The polynucleotide includes not only nucleotide sequences that encode amino acid sequences of the protein complex, but also complementary sequences thereof. The complementary sequences include sequences that are perfectly complementary, as well as sequences that are substantially complementary. Under stringent conditions known to one of ordinary skill in the art, the polynucleotide may be sequences that may be hybridized with the nucleotide sequences that encode amino acid sequences of the protein complex.

In addition, the nucleotide sequences that encode amino acid sequences of the protein complex may be changed. The change includes to an addition, an insertion, or a deletion of the nucleotides, or a non-conservative substitution or a conservative substitution. The polynucleotide that encodes the amino acid sequence of the protein complex may include nucleotide sequences that represent a substantial identity with the nucleotide sequences described above. When the nucleotide sequences are aligned as much as possible to correspond to any other sequences, and the aligned sequences are analyzed by using the algorithm known to one of ordinary skill in the art, the sequences representing a substantial identity may refer to sequences having at least 80% identity/homology, at least 90% identity/homology, or at least 95% identity/homology (e.g., at least 96% identity/homology, at least 97% identity/homology, at least 98% identity/homology, at least 99% identity/homology, or 100% identity/homology).

According to another embodiment of the present invention, the polynucleotide may comprise, consist essentially of, or consist of the nucleotide sequence of SEQ ID NO: 16 or SEQ ID NO: 18.

According to another aspect of the present invention, a recombinant vector comprising the polynucleotide and a promoter that is operatively linked with the polynucleotide is provided, wherein the polynucleotide encodes the protein complex.

The terminology "vector" used herein refers to the means for expressing target gene expression in a host cell. For example, the vector may include a plasmid vector, a cosmid vector, and a viral vector, such as a bacteriophage vector, an adenovirus vector, a retrovirus vector, and an adeno-associated virus vector. The recombinant vectors may be prepared by modifying the following: a plasmid (e.g., pSC101, pGV1106, pACYC177, ColE1, pKT230, pME290, pBR322, pUC8/9, pUC6, pBD9, pHC79, pIJ61, pLAFR1, pHV14, a series of pGEX, a series of pET and pUC19, etc), a phage (e.g., λgt4λB, λ-Charon, λΔz1 and M13, etc), or a virus (e.g., SV40, etc), which are known in the art.

In the recombinant vector, the polynucleotide that encodes the protein complex may be operatively linked to the promoter. The terminology "operatively linked" used herein refers to a functional binding between nucleotide expression regulatory sequences (e.g., promoter sequences) and other nucleotide sequences. Therefore, the regulatory sequences may regulate the transcription and/or translation of the other nucleotide sequences.

The recombinant vector may be a recombinant vector for cloning or a vector for gene expression. The vector for gene expression may be a vector that is normally used in the art for gene expression of the foreign protein from plants, animals, or microorganisms. The recombinant vector may be prepared through a variety of methods known to one of ordinary skill in the art.

The invention also provides a host cell comprising the polynucleotide or vector. The host cell may be a prokaryotic cell or a eukaryotic cell. For example, when using a vector that is designed for gene expression a prokaryotic cell as the host cell, the vector usually includes a strong promoter enabling a transcription (e.g., pL promoter, trp promoter, lac promoter, tac promoter, T7 promoter, etc), a ribosome-binding site for translation, and a transcription/translation terminator sequence. When the host cell is a eukaryotic cell, a replication origin in the vector operating in the eukaryotic cell may include f1 replication origin, SV40 replication origin, pMB1 replication origin, adeno replication origin, AAV replication origin, BBV replication origin, or the like, but the replication origins are not limited to the above-described examples. In addition, a promoter derived from the genome of mammalian cells (e.g., methallothionein promoter) or a promoter derived from the genome of mammalian viruses (e.g., adenoviral late promoter, vaccinia virus 7.5K promoter, SV40 promoter, cytomegalovirus promoter, and tk promoter of HSV) may be used, and the vector typically has polyadenylation sequences as transcription terminator sequences.

The vector that may express the protein complex may be operated based on a vector system in which the first fusion protein and the second fusion protein are simultaneously expressed therein, or in which the first fusion protein and the second fusion protein are expressed in two different vectors separately. In the latter case, the two different vectors may be introduced into host cells through co-transformation or targeted transformation.

According to another aspect of the present invention, a host cell comprises the recombinant vector that comprises the polynucleotide and the promoter operatively linked to the polynucleotide.

A host cell that may be used to clone or express stably and subsequently the recombinant vector may be any host cell known to one of ordinary skill in the art. Examples of the prokaryotic host cells are *E. coli* JM109, *E. coli* BL21, *E. coli* RR1, *E. coli* LE392, *E. coli* B, *E. coli* X 1776, *E. coli* W3110, *Bacillus* sp. such as *Bacillus subtilis* and *Bacillus thuringiensis*, or enterobacteria such as *Salmonella typhimurium, Serratia marcescens*, and various *Pseudomonas* sp. When transformation occurs in an eukaryotic cell, a host cell may be used from *Saccharomyces cerevisiae*, insect cells, plant cells, and animal cells, cell lines such as Sp2/0, Chinese hamster ovary (CHO) K1, CHO DG44, PER.C6, W138, BHK, COS-7, 293, HepG2, Huh7, 3T3, RIN, and MDCK.

Transport into the host cell of the polynucleotide or the recombinant vector comprising the polynucleotide may use methods known to one of ordinary skill in the art. For example, in the case of the prokaryotic host cells, $CaCl_2$ methods, electroporation, or the like may be used. In the case of the eukaryotic host cells, methods of microinjection, calcium phosphate precipitation, electroporation, ribosome-mediated transfection, gene bombardment, or the like may be used, but are not limited thereto.

A method of screening the transformed host cells may be carried out easily according to the methods known to one of ordinary skill in the art by using the phenotype of a selectable marker. For example, when a selectable marker is a resistance gene to a specific antibiotic, a transformant may be selected easily by culturing the transformant in a medium containing the antibiotic.

According to another aspect of the present invention, a method of manufacturing a bispecific antibody includes a process to produce the first and the second fusion proteins by expressing the recombinant vector that comprises the polynucleotide that encodes the protein complex and the promoter that is operatively linked to the polynucleotide.

The method of preparing the bispecific antibody may be performed in vivo or in vitro.

In the case of a bispecific antibody prepared in vivo, when the first and the second fusion proteins are produced by expressing the recombinant vector within the cells, the first and the second fusion proteins may be secreted to the outside of the cells in the form of a complete bispecific antibody. For example, the first and the second fusion proteins initiate translation within the cells at the same time as transporting to endoplasmic reticulum (ER). The translation of the first and the second binding protein within the endoplasmic reticulum may terminate in ER, then the first and the second binding proteins may be present in the adjacent position to the first and the second fusion proteins due to complementary binding between the first and the second binding proteins. Accordingly, the first and the second polypeptides may voluntarily form a dimer to form the bispecific antibody. Thereafter, through a Golgi apparatus, the first and the second binding proteins may form the bispecific antibody in a complete form by cleaving amino acid sequences between the first binding protein and the first polypeptide, or between the second binding protein and the second polypeptide using proteases in the Golgi apparatus. A bispecific antibody formed in such a manner may be purified according to the purification methods known to one of ordinary skill in the art.

In the case of a bispecific antibody manufactured in vitro, when the first and the second binding proteins are expressed together within the cells, the first and the second fusion proteins form the bispecific antibody by specific binding therebetween within the host cell, and they are secreted to the outside of the host cell.

According to another embodiment of the present invention, the separation process may be carried out by adding proteases that recognize amino acid sequences enabling cleavage. The amino acid sequences that enable cleavage may be TEV-cleavage peptides or furin-cleavage peptides. Namely, the bound first and second fusion proteins may be cleaved by TEV protease or furin protease, and then the first and second polypeptides may be separated from the fusion proteins to form the bispecific antibody.

Hereinafter, one or more embodiments of the present invention will be described in detail. However, these examples are presented herein for illustrative purpose only and the present invention is not limited thereto.

Figure 1A:
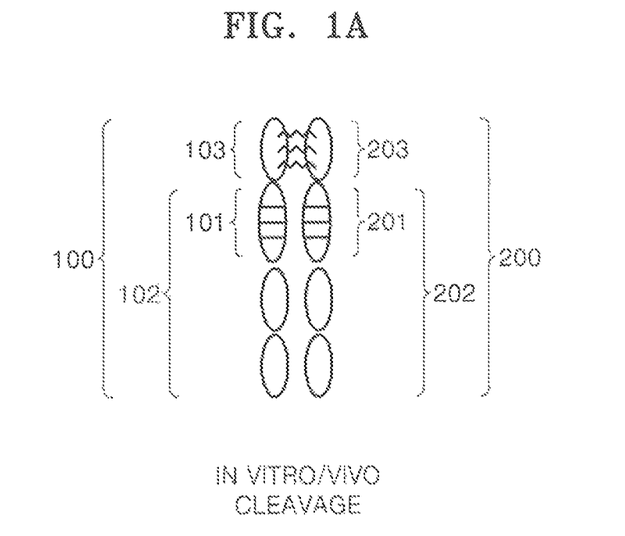
FIGS. 1A and 1B are schematic views illustrating a protein complex and a method of preparing a bispecific antibody using the protein complex, according to an embodiment of the present invention.
Figure 1B:
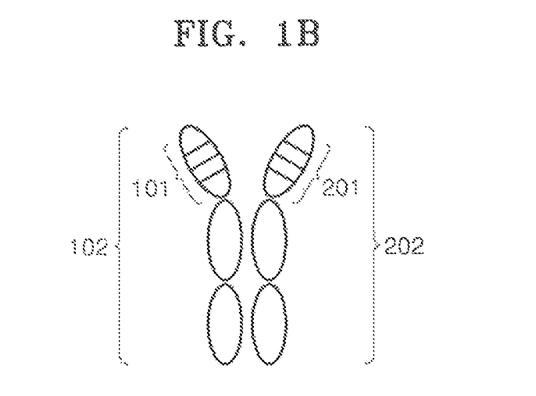

FIG. 1 is a schematic view illustrating a protein complex that is composed of a first fusion protein and a second fusion protein each including a different antigen-binding site, according to an embodiment of the present invention. As shown in FIG. 1, a first polypeptide 102 including a first antigen-binding site 101 and a second polypeptide 202 including a second antigen-binding site 201 include a first binding protein 103 and a second binding protein 203 that are linked to the terminus of the first polypeptide 102 and the second polypeptide 202, respectively. The first binding protein 103 and the second binding protein 203 are composed of proteins that may specifically interact with each other (for example, GABAR1 and GABAR2 that may form a heterodimer). The first and second binding proteins 103 and 203 are each included in a first fusion protein 100 and a second fusion protein 200, respectively. Thus the first fusion protein 100 and the second fusion protein 200 exist as a combined state in vivo or in vitro, as shown in FIG. 1A. Peptides (e.g., furin cleavage peptides) that may enable cleavage are included between the first binding protein 103 and the first polypeptide 102 and between the second binding protein 203 and the second polypeptide 202. Thus, when the peptides that may enable cleavage at these locations are cleaved, the first binding protein 103 and the second binding protein 203 that are cleaved in vitro or in vivo are released from the first fusion protein 100 and the second fusion protein 200, respectively. The first fusion protein 100 and the second fusion protein 200 then may be bound to each other through a completely voluntary combination to form a bispecific protein complex including the first antigen-binding site 101 and the second antigen-binding site 201 (see FIG. 1B).

Example 1

Preparations of Expression Vectors for Fusion Proteins

In order to produce two kinds of fusion proteins, two kinds of expression vectors were prepared from GeneArt® (Life Technology Corp.). The first fusion protein (GABAR1-VEGF2) was linked in the order of a secretion signal sequence, gamma-aminobutyic acid receptor type 1 (GABAR1), a furin cleavage peptide, a single-domain antibody including a binding site of vascular endothelial growth factor (VEGF) protein, and an Fc domain including a hinge (hinge-CH2-CH3). The second fusion protein (GABAR2-EGFR2) was linked in the order of a secretion signal sequence, gamma-aminobutyric acid receptor type 2 (GABAR2), a furin cleavage peptide, a single-domain antibody including a binding site of epidermal growth factor receptor (EGFR) protein, and an Fc domain including a hinge. Amino acid sequences to prepare the two fusion proteins and nucleotide sequences that encode the amino acid sequences are listed in Table 1.

TABLE 1

|  | Amino acid sequence | Nucleotide sequence |
| --- | --- | --- |
| Secretion signal sequence | MGWSCIILFLVATATGVHS (SEQ ID NO: 1) | SEQ ID NO: 2 |
| GABAR1 | EAQDTMKTGSSTNNNEEEKSRLLEKEN RELEKIIAEKEERVSELRHQLQSRQQLR SRRH (SEQ ID NO: 3) | SEQ ID NO: 4 |

TABLE 1-continued

| | Amino acid sequence | Nucleotide sequence |
|---|---|---|
| GABAR2 | VNQASTSRLEGLQSENHRLRMKITELD KDLEEVTMQLQDTPEKTTYIK (SEQ ID NO: 5) | SEQ ID NO: 6 |
| Furin cleavage peptide | RGRKRR (SEQ ID NO: 7) | SEQ ID NO: 8 |
| Anti-VEGF2 single-domain antibody | DIQMTQSPSSLSASVGDRVTITCRASQK IFNGLSWYQQKPGKAPKLLIYHSSTLQS GVPSRFSGSGSGTDFTLTISSLQPEDFA TYYCQQVLLYPYTFGQGTKVEIKR (SEQ ID NO: 9) | SEQ ID NO: 10 |
| Anti-EGFR2 single-domain antibody | DIQMTQSPTSLSASVGDRVTITCRASQ WIGNLLDWYQQKPGEAPKLLIYYASFLQ SGVPSRFSGGGFGTDFTLTISSLQPEDF ATYYCQQANPAPLTFGQGTKVEIKR (SEQ ID NO: 11) | SEQ ID NO: 12 |
| Hinge-CH2—CH3 | EPKSCDKTHTCPPCPAPELLGGPSVFL FPPKPKDTLMISRTPEVTCVVVDVSHED PEVKFNWYVDGVEVHNAKTKPREEQY NSTYRVVSVLTVLHQDWLNGKEYKCKV SNKALPAPIEKTISKAKGQPREPQVYTL PPSREEMTKNQVSLTCLVKGFYPSDIAV EWESNGQPENNYKTTPPVLDSDGSFFL YSKLTVDKSRWQQGNVFSCSVMHEAL HNHYTQKSLSLSPGK (SEQ ID NO: 13) | SEQ ID NO: 14 |
| Fusion protein of GABAR1-furin cleavage peptide-anti-VEGF2-hinge-CH2—CH3 | EAQDTMKTGSSTNNEEEKSRLLEKEN RELEKIIAEKEERVSELRHQLQSRQQLR SRRHRGRKRRDIQMTQSPSSLSASVGD RVTITCRASQKIFNGLSWYQQKPGKAP KLLIYHSSTLQSGVPSRFSGSGSGTDFT LTISSLQPEDFATYYCQQVLLYPYTFGQ GTKVEIKREPKSCDKTHTCPPCPAPELL GGPSVFLFPPKPKDTLMISRTPEVTCVV VDVSHEDPEVKFNWYVDGVEVHNAKT KPREEQYNSTYRVVSVLTVLHQDWLNG KEYKCKVSNKALPAPIEKTISKAKGQPR EPQVYTLPPSREEMTKNQVSLTCLVKG FYPSDIAVEWESNGQPENNYKTTPPVL DSDGSFFLYSKLTVDKSRWQQGNVFS CSVMHEALHNHYTQKSLSLSPGK (SEQ ID NO: 15) | SEQ ID NO: 16 |
| Fusion protein of GABAR2-furin cleavage peptide-anti-EGFR2-hinge-CH2—CH3 | VNQASTSRLEGLQSENHRLRMKITELD KDLEEVTMQLQDTPEKTTYIKRGRKRR DIQMTQSPTSLSASVGDRVTITCRASQ WIGNLLDWYQQKPGEAPKLLIYYASFLQ SGVPSRFSGGGFGTDFTLTISSLQPEDF ATYYCQQANPAPLTFGQGTKVEIKREP KSCDKTHTCPPCPAPELLGGPSVFLFP PKPKDTLMISRTPEVTCVVVDVSHEDPE VKFNWYVDGVEVHNAKTKPREEQYNS TYRVVSVLTVLHQDWLNGKEYKCKVSN KALPAPIEKTISKAKGQPREPQVYTLPP SREEMTKNQVSLTCLVKGFYPSDIAVE WESNGQPENNYKTTPPVLDSDGSFFLY SKLTVDKSRWQQGNVFSCSVMHEALH NHYTQKSLSLSPGK (SEQ ID NO: 17) | SEQ ID NO: 18 |

In order to prepare the two fusion proteins, vectors were designed to include an EcoRI restriction enzyme recognition site located at the 5' end of a DNA fragment that encodes the fusion proteins and an XhoI restriction enzyme recognition site at the 3' end of the DNA fragment. Herein, the vectors for protein overexpression used pcDNA 3.1 myc/his A (Invitrogen).

Example 2

Expression and Purification of the Fusion Proteins, and Confirmation of Protein Complexes In order to overexpress the two fusion proteins by using the vectors prepared according to Example 1, human embryonic growth cells HEK293-F (Korean Cell Line Bank) that were transformed with the vectors described above were used. HEK293-F cells were maintained inside an orbital shaker under the conditions of 37° C., 130 rpm, and 8% $CO_2$. For the transformation, the cells were separated from a medium by centrifugation, and then about $1 \times 10^6$ cells were suspended in Freestyle 293 Expression media (Invitrogen). In addition, by using FreeStyle™ MAX reagent (Invitrogen), the HEK293-F cells were transformed with 100 μg of the vectors. About 7 to 8 days after the transformation, the supernatant was collected by centrifugation (4000×g, 10 min, 4° C.) and filtered using a 0.22 micron pore size filter. Such obtained supernatant was used for purification of the fusion proteins.

The fusion proteins were separated by protein A affinity column (GE Healthcare). First, the protein A affinity column was equilibrated with 1×PBS (Invitrogen) solution, the supernatant was added into the equilibrated protein A affinity column, then the column was washed out with a washing buffer solution (1×PBS), which was equivalent to 5 times the column volume, and finally, the fusion protein was eluted by an elution buffer containing 10% glycerol (IgG elution buffer, Thermo Scientific). The eluted solution was immediately neutralized by 1 M Tris-HCl (pH 9.0) solution. The eluted solution obtained from the protein A affinity column was added to a desalting column (GE Healthcare) that was equilibrated with a 25 mM MES (pH 6.0) solution. A sample was made by collecting the eluted proteins having the changes in absorbance at UV 280 nm while the equilibrated solution was added into the column. The protein sample was added into a Mono S column (GE Healthcare) that was equilibrated with the equilibrating solution. Proteins that were not bound to the column used were eliminated by adding the equilibrating solution, and proteins that were bound to the column were eluted by increasing a concentration of salt from about 0 mM to about 250 mM in a washing solution of 25 mM MES and salt (NaCl). Fractions containing the fusion proteins were confirmed through the absorbance at 280 nm and SDS-PAGE, and the fractions were collected and concentrated by using an Amicon Ultra-15 Centrifugal Filter (Millipore). Concentration of the purified proteins was measured by using BSA as standard materials.

Thereafter, the protein complex was confirmed using SDS-PAGE. Before loading to gel, the protein complex was divided into two to treat one division with 1 mM β-mercaptoethanol and the other division without β-mercaptoethanol, and then the protein complex was loaded onto the gel. As a result, it was confirmed that a single-domain antibody including a binding site of VEGF and a single-domain antibody including a binding site of EGFR is the form of a monomer (in the division treated with (β-mercaptoethanol).

Example 3

Confirmation of Bispecific Antigen-Antibody Reactions of the Protein Complex

In order to measure binding affinity of the bispecific antigen-antibody reaction of the protein complex that was prepared according to Example 2, BiacoreT100 instrument (GE healthcare) was used to perform a Surface Plasmon resonance assay. 1×HBS-EP (GE healthcare) was used as a running buffer and a dilution buffer. Anti-human IgG antibodies (Jackson Immuno Research) were fixed on a surface of a CM5 chip (GE Healthcare) in about 5000 response units (RUs) by the standard amine-coupling reaction. About 500 RUs of the protein complex were flowed to bind to the chip surface, and then the extracellular domain (ProSpec) of human EGFR or human VEGF (Pangen) in several concentrations (6.25~100 nM) were flowed at a rate of 50 μL/min. The association phase was about 180 seconds, and the dissociation time (washing out with a running buffer solution) was about 600 seconds. After finishing each of the binding cycles, a regenerating solution, Glycine-HCl pH 2.0 (GE healthcare), was flowed at a rate of 50 μL/min for about 1 minute to eliminate the bound antigen and the bound antibody from the chip surface. The Sensogram obtained in such a manner used a 1:1 Langmuir binding model (in the case of EGFR) and a bivalent analyte model (in the case of VEGF) to perform a fitting in BIA evaluation software. The results are shown in FIG. 2.

Figure 2:
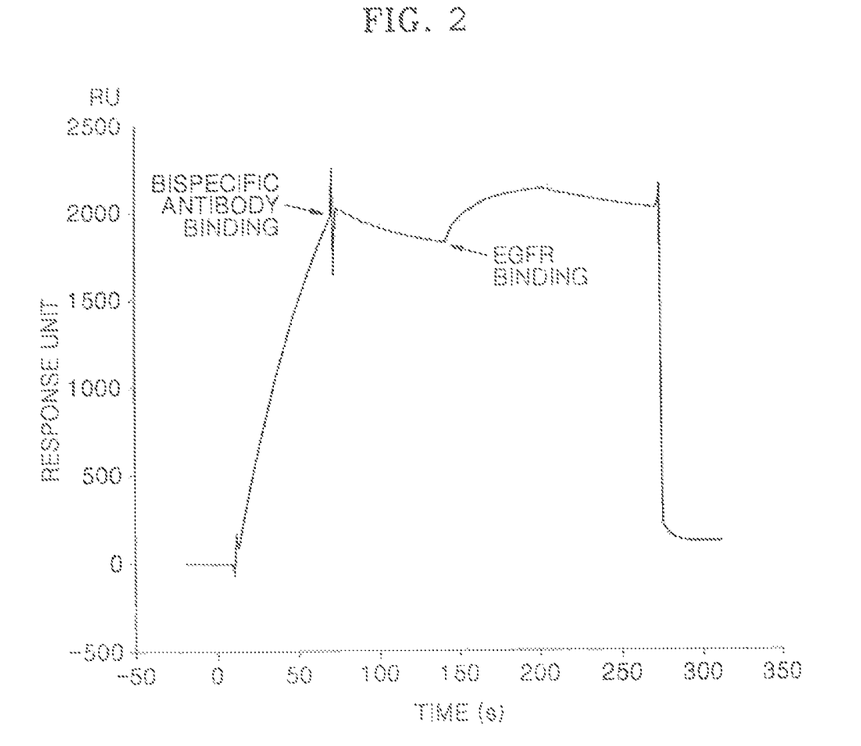
FIG. 2 illustrates a result of sensorgram showing effect of a bispecific antigen-antibody reaction of the protein complex, wherein response unit (RU) is indicated on the y-axis and time (seconds) is indicated on the x-axis, according to an embodiment of the present invention.

As shown in FIG. 2, it was confirmed that the protein complex prepared according to Examples 1 and 2 specifically recognized both VEGF and EGFR.

As described above, according to the one or more embodiments of the present invention, the use of the inventive protein complex allows the more efficient preparation of a bispecific antibody relative to conventional methods.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A protein complex comprising:
   (i) a first fusion protein comprising (a) a first polypeptide that comprises a first antigen-binding site and (b) a first binding protein linked to the N-terminus of the first polypeptide and located at the N-terminus of the first fusion protein; and
   (ii) a second fusion protein comprising (a) a second polypeptide that comprises a second antigen-binding site and (b) a second binding protein linked to the N-terminus of the second polypeptide and located at the N-terminus of the second fusion protein,
   wherein the protein complex comprises an amino acid sequence that enables cleavage between the first polypeptide and the first binding protein, or between the second polypeptide and the second binding protein, or wherein the protein complex comprises both an amino acid sequence that enables cleavage between the first polypeptide and the first binding protein, and an amino acid sequence that enables cleavage between the second polypeptide and the second binding protein,
   wherein the first antigen-binding site and the second antigen-binding site specifically bind different antigens, and
   wherein the first binding protein and the second binding protein specifically bind to each other.

2. The protein complex of claim 1, wherein the first antigen-binding site and the second antigen-binding site are positioned at the N-terminus of the first polypeptide and the second polypeptide, respectively.

3. The protein complex of claim 1, wherein the first binding protein and the second binding protein form a heterodimer.

4. The protein complex of claim 3, wherein the first binding protein and the second binding protein that form the heterodimer are GABAR1 and GABAR2; Jun and Fos; Lin7 and Lin2C; c-Myc and Max; ATF4 and EBP; Pop5 and Rpp1; ErbB1 and ErbB2; RXR and PPARγ; RXR and TR; AP3 and PI; MDM2 and MDMX; SRP9 and SRP14; p50 and p65; TLR1 and TLR2; IMβ and IM7; TAP and p15; or p40 and p67.

5. The protein complex of claim 1, wherein the polypeptide comprising the antigen-binding site comprises a single-domain antibody, Fab2-Fc, scFv-Fc, Ab-Fc domain, a nanobody, a minibody, a type of IgG, an Fc region, or a combination thereof.

6. The protein complex of claim 1, wherein amino acid sequences that enable cleavage are TEV-cleavage peptides or furin-cleavage peptides.

7. The protein complex of claim 1, wherein the amino acid sequences that enable cleavage are selected from the group consisting of SEQ ID NO:19 to SEQ ID NO:25.

8. The protein complex of claim 1 comprising the amino acid sequence of SEQ ID NO: 15 or 17.

9. A polynucleotide that encodes the protein complex of claim 1.

10. The polynucleotide of claim 9, wherein the polynucleotide comprises SEQ ID NO: 16 or 18.

11. The polynucleotide of claim 9, wherein the polynucleotide encodes SEQ ID NO: 15 or 17.

12. A recombinant vector comprising the polynucleotide of claim 9.

13. A method of preparing a bispecific antibody comprising
   producing a first fusion protein and a second fusion protein by expressing a recombinant vector comprising a polynucleotide that encodes the protein complex of claim 1 and a promoter that is operatively connected polynucleotide that encodes the protein complex.

14. The method of claim 13, wherein the first binding protein and the second binding protein form a heterodimer in a cell, and the heterodimer is secreted outside the cell.

15. The method of claim 13, further comprising separating the first binding protein and the second binding protein from the first fusion protein and the second fusion protein, respectively.

16. The method of claim 15, wherein the separation is performed by adding a protease that recognizes the amino acid sequences that enable cleavage.

17. The method of claim 16, wherein the protease is furin, calpain, factor X (FXa), tobacco etch virus (TEV) protease, proprotein convertase (PC) family, or a combination thereof.

* * * * *